US010646151B2

(12) United States Patent
Lefever et al.

(10) Patent No.: US 10,646,151 B2
(45) Date of Patent: May 12, 2020

(54) EXERCISE SYSTEM AND METHOD

(71) Applicant: KATHOLIEKE UNIVERSITEIT LEUVEN, Leuven (BE)

(72) Inventors: Joris Lefever, Herent (BE); Daniel Berckmans, Kessel-Lo (BE); Vasileios Exadaktylos, Kessel-Lo (BE); Jean-Marie Aerts, Haasrode (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 47 days.

(21) Appl. No.: 14/379,079

(22) PCT Filed: Feb. 18, 2013

(86) PCT No.: PCT/BE2013/000008
§ 371 (c)(1),
(2) Date: Aug. 15, 2014

(87) PCT Pub. No.: WO2013/120151
PCT Pub. Date: Aug. 22, 2013

(65) Prior Publication Data
US 2015/0327804 A1    Nov. 19, 2015

(30) Foreign Application Priority Data
Feb. 16, 2012   (GB) .................................. 1202637.3

(51) Int. Cl.
*A61B 5/22* (2006.01)
*A63B 24/00* (2006.01)
(Continued)

(52) U.S. Cl.
CPC ............ *A61B 5/222* (2013.01); *A61B 5/0205* (2013.01); *A61B 5/1118* (2013.01); *A61B 5/486* (2013.01);
(Continued)

(58) Field of Classification Search
None
See application file for complete search history.

(56) References Cited

U.S. PATENT DOCUMENTS 5,691,452 A * 11/1997 Gawryl .................... A01N 1/02
530/385
5,853,351 A    12/1998 Maruo et al.
(Continued)

FOREIGN PATENT DOCUMENTS

| EP | 1127543 A1 | 8/2001 |
|----|------------|--------|
| WO | 2008003148 A1 | 1/2008 |
| WO | 2009133248 A1 | 11/2009 |

OTHER PUBLICATIONS

Conconi et al., "Determination of the Anaerobic Threshold by a Noninvasive Field Test in Runners," Journal of Applied Physiology, 1982, pp. 869-873, vol. 52, No. 4.
(Continued)

*Primary Examiner* — Kaylee R Wilson
*Assistant Examiner* — Jairo H Portillo
(74) *Attorney, Agent, or Firm* — Workman Nydegger

(57) ABSTRACT

We here describe an exercise system and control method thereof to obtain exercise protocols relating to the individual user's optimal exercise intensity. The system and method comprise the monitoring of the transition between the aerobic and anaerobic training zones and an estimate of the maximal lactate steady state, which is an important physiological indicator of the user's cardio respiratory fitness. Together with individual models of how the user's heart rate responds to exercise intensity, it is possible to predict the needed exercise intensity that should be performed to obtain the wanted exercise goal. The analysis can (preferably) be performed in real-time during exercise.

8 Claims, 5 Drawing Sheets

(51) Int. Cl.
*A61B 5/11* (2006.01)
*A61B 5/00* (2006.01)
*A61B 5/0205* (2006.01)
*G06F 19/00* (2018.01)
*A61B 5/024* (2006.01)
*G16H 50/50* (2018.01)

(52) U.S. Cl.
CPC .......... *A61B 5/4866* (2013.01); *A61B 5/7275* (2013.01); *A61B 5/7278* (2013.01); *A63B 24/0062* (2013.01); *G06F 19/3481* (2013.01); *A61B 5/024* (2013.01); *A63B 2220/00* (2013.01); *G16H 50/50* (2018.01)

(56) References Cited

U.S. PATENT DOCUMENTS

| | | | | |
|---|---|---|---|---|
| 2001/0027266 | A1* | 10/2001 | Hautala | A61B 5/222 600/16 |
| 2003/0093129 | A1* | 5/2003 | Nicolelis | A61B 5/0478 607/45 |
| 2005/0043894 | A1* | 2/2005 | Fernandez | A61B 5/0215 702/19 |
| 2005/0164832 | A1 | 7/2005 | Maschke | |
| 2006/0079800 | A1* | 4/2006 | Martikka | A61B 5/0488 600/546 |
| 2008/0146890 | A1* | 6/2008 | LeBoeuf | A61B 5/0059 600/300 |
| 2009/0024013 | A1* | 1/2009 | Soller | A61B 5/14551 600/324 |
| 2009/0312150 | A1 | 12/2009 | Wu | |
| 2010/0217142 | A1* | 8/2010 | Klepp | A61B 5/0452 600/520 |
| 2012/0101402 | A1* | 4/2012 | Nguyen | A61B 5/7264 600/544 |

OTHER PUBLICATIONS

Grazzi et al., "The Power Output/Heart Rate Relationship in Cycling: Test Standardization and Repeatability," Medicine and Science in Sports and Exercise, Oct. 1999, pp. 1478-1483, vol. 31, No. 10.
Hoogeveen et al., "The Ventilatory Threshold, Heart Rate, and Endurance Performance: Relationships in Elite Cyclist," International Journal of Sports Medicine, 1999, pp. 114-117, vol. 20, No. 2.
International Search Report for corresponding International PCT Application No. PCT/BE2013/000008, dated Jul. 25, 2013.
Van Schuylenbergh et al., "Correlations Between Lactate and Ventilatory Thresholds and the Maximal Lactate Steady State in Elite Cyclist," International Journal of Sports Medicine, 2004, pp. 403-408, vol. 25, No. 6.

* cited by examiner

EXERCISE SYSTEM AND METHOD

FIELD OF THE INVENTION

The present invention generally relates to exercise systems to improve the physical performance of a training person, as well as control methods thereof. Particularly, the systems and methods according to the present invention comprise monitoring and/or determining in real-time the aerobic and anaerobic phase during training and exercise. This real-time monitoring, estimation and/or prediction of the individual's cardio respiratory fitness can be used to adapt and optimise exercise protocols to reach the wanted exercise goal as efficiently as possible.

BACKGROUND OF THE INVENTION

The lactate concentration in the blood is one of the important substances formed during an exercise and the formation is depending on the athlete's cardio respiratory fitness. It is used to determine the transition between the aerobic and anaerobic energy delivery system (=lactate threshold). The lactate threshold (LT) or anaerobic threshold (i.e., the point at which the subject can no longer provide all of the energy necessary to perform that workload with only aerobic metabolism) or more specifically, the maximal lactate steady state (MLSS) is a measure for the current cardio respiratory fitness of the individual athlete. It is defined as the highest exercise intensity that can be maintained for extended periods of time. At exercise intensities above the anaerobic threshold, carbohydrates are anaerobically metabolized into lactic acid, as opposed to pyruvate under aerobic metabolism. While the body is able to clear (i.e., metabolize) some lactic acid, a point is eventually reached whereby the lactic acid begins to accumulate in the muscles and bloodstream, eventually causing muscle soreness and fatigue.

Knowledge of the transition between the aerobic and the anaerobic training zone is an essential aspect in many training protocols and for monitoring the total training intensity, including in training protocols for amateur athletes or professional athletes, in exercise schedules in fitness centres or in the rehabilitation process of many thousands of patients. Long training sessions in the anaerobic training zone will impose a heavy training load on the athlete. This means that he will not be able to sustain this training level for a long time. This is unwanted particularly during endurance training. Endurance training protocols generally comprise of long hours of exercise at an aerobic level. A simple, yet accurate, method for monitoring the exercise level will be a great addition to training soft- and hardware, because it makes training protocols, where a clear distinction between aerobic and anaerobic training zones is necessary, easier to complete.

Today, the numbers of entries in the fitness centres are skyrocketing. The reason is the experience of the positive impact of a healthy body on the quality of life (Mens sana in corpore sano). Many people are forced to follow that rule, because they suffer from disease of civilization such as obesity, cardiovascular diseases . . . . However, not many people from that large group complete their exercise, because their busy schedule does not allow for extensive exercise schedules in fitness centres or because their condition is not improving fast enough for them to notice. This is due to the fact that the exercise schedules do not target the individual. Individual exercise guidance will lead to a shorter workout with better results, making the people more inclined to finish the exercise. This gives people also more perseverance, because the exercise is specifically made for them instead for another. To optimize their individual exercise, an accurate estimate of their cardio respiratory fitness is necessary. The test should be simple and short, so that they can perform the test each day before the exercise and preferably during the warming-up.

Different types of exercise also play an important role in the rehabilitation process of many thousands of patients (Expenditure of the Belgian RIZIV 2008: 340 Million Euro, http://riziv.fgov.be), and the specific physical guidance of a significant group of physically disabled people. Currently, the majority of those patients go through (depending on the disorder) empirical standard therapeutic exercise regimens in which limited attention is given to their individual response to exercise. The cost of rehabilitation is substantial, so that significantly shorter and optimal rehabilitation will be cost efficient for the health insurance. Some specific rehabilitation protocols that use ergo meters can be optimized if the current cardio respiratory fitness can be determined in a correct and easy way.

Determination of Cardio Respiratory Fitness

Many tests to assess the cardio respiratory fitness of people are known.

Many amateur athletes use predefined heart rate levels to train. These levels are defined in percentages of their maximal heart rate (HRMax). The common rule to define the HRMax is:

HRMax=220−age, but also other generic rules are used.

However, these rules are established at population level. They lead to exercise protocols which are far from optimal, because they do not take the individual and time-variant aspect of cardio respiratory fitness into account.

Professional athletes actually measure their cardio respiratory fitness by measuring their LT with a step test until exhaustion. This test is currently regarded as the reference measurement for determining cardio respiratory fitness. This test is very comprehensive and requires expertise to implement, because lactate measurements should be executed. The earlobe is pricked in this invasive test to obtain a droplet of blood in which the lactate concentration is determined. This test is only performed a few times a year (every four to six weeks), because it has negative effects on the body of the professional athlete if the test is performed too often. The problem is that the cardio respiratory fitness can vary in the period between two of those tests.

The LT is an important variable in sports physiology. The LT is well documented in the literature, but is defined in many different ways. The only accurate way to determine the LT is to measure the MLSS. This requires several exercise tests performed over a span of 1 to 2 weeks [Van Schuylenbergh, et al., International Journal of Sports Medicine, 2004, 25(6), 403-408]. This is a very elaborate process and impractical for professional athletes. Therefore many sports physiologists try to estimate the LT with other physiological variables that are easier to measure. For this purpose lactate and respiratory measurements are used. Conconi [Conconi et al., Journal of Applied Physiology, 1982, 52(4), 869-873] developed a non invasive test for determining the anaerobic threshold for runners. He used the inflection point in the relationship between speed and heart rate during running as estimator for the anaerobic threshold. This study was repeated for cyclists, where the relationship between power and heart rate was used [Grazzi et al., Medicine and Science in Sports and Exercise, 1999, 31(10)

1478-1483]. The Conconi test is widely used although the test is very controversial, because a clear inflection point is not always observed. Furthermore, the inflection point depends on the test protocol.

Sub-maximal tests are also used to estimate the cardio respiratory fitness, but they are not as accurate as the step test until exhaustion.

Some fitness systems use a measured or estimated physical parameter to control the exercise (US2009/0312150, WO2009/133248). They control the exercise by linking the relative intensity of an exercise to the physical parameter, namely the heart rate, in order to obtain an optimal exercise level. However, current state-of-art does not take into account that the physical response to exercise intensity is individually different for every individual. This could cause problems when exercise protocols are made. Also, current state-of-art does not use the absolute exercise intensity indicator. So, the exercise intensity could be over- or underestimated, which will resolve in inefficient exercise protocols.

EP1127543 describes method and systems to assess the lactate concentration in a human body in connection with exercise using a mathematical model, implemented as a neural network which relates heart rate information with lactate concentration by a stress level, defined as the quantity of performed exercise intensity during the last hour. Since training using data from many hundreds or thousands of persons is an essential feature of this neural network, this method again is based on on statistical relationships taken from a population of many individuals. In reality however no living organism is acting or behaving as an average of a population, but instead as an individual, dynamic and time-varying system, which does not respond in a standard way. A neural network solution can hence never be more accurate than the standard deviation around the theoretical average and for living organisms this ends up in a high error for each individual at a given moment.

Thus, the currently used tests to determine cardio respiratory fitness or measure exercise intensities are often elaborate and/or inaccurate, are insufficiently adapted to the individual training person or are difficult to use in real-time. Indeed, the lactate threshold is varying in time for an individual, depending on his physical condition.

Thus, there is a need in the art for a more accurate, simpler, short, individualised exercise system and control method thereof that monitors, determines and estimates or predicts the transition between the aerobic and anaerobic training zone, and thus also the cardio respiratory fitness.

SUMMARY OF THE INVENTION

The present invention addresses the drawbacks of the prior art and relates to a system and methods that use knowledge of the real-time and individual heart rate response to the intensity of an activity, training or exercise (based on a data based modelling technique) to predict how the body of an individual living organism, particularly an individual human, with a specific cardio respiratory fitness, will react on a certain activity impulse. This way, an individualized optimal exercise protocol can be made to obtain efficient exercise. The present non-invasive system and method can be used each day, e.g. before the actual exercise and preferably during the warming-up and/or during the daily activities, like walking up the stairs, carrying a load, etc.

The present invention provides methods and systems for evaluating and controlling the cardio respiratory fitness of an individual living organism comprising the use of a data based modelling technique (relating the heart response of said individual to the exercise intensity) to determine, estimate and predict important biological and physiological variables, particularly the lactate threshold (LT), of the exercising individual. Thus, in the present invention the transition between the aerobic and anaerobic training zones is monitored and/or predicted without having to perform the actual lactate measurements.

Preferably, the methods and systems of the present invention further comprise measuring the heart rate of the exercising living organism. In one aspect of the present invention, the methods and systems of the present invention comprise the estimation and prediction of LT in real time by detecting the dynamic change of the heart rate response to exercise or activity intensity that occurs when the exercising living organism (human) exceeds his personal LT. Or stated differently, in the present invention an individual model is developed for every individual of how his heart rate responds to exercise intensity. Based on the knowledge of the individual cardio respiratory fitness, it is possible to predict how the heart rate will respond to a certain exercise. This allows preparing optimal exercise schedules in order to achieve an effective workout or training Preferably, the methods and systems of the present invention further comprise providing feedback to the exercising individual to adjust the exercise intensity to better fit his physical condition or training goal.

The present invention thus generally relates to methods and systems for the development and implementation of unique exercise regimes, and more particularly, methods and systems for developing customized cardio respiratory fitness and endurance exercise programs for individuals.

The methods and systems of the present invention can be used by all individuals that want to improve their cardio respiratory fitness, including the casual exercising person, and athletes of amateur or professional level, but it can also be used for revalidation purposes that require aerobic fitness exercise. It can also be used in training animals, such as horses.

A preferred embodiment of the present invention relates to a system for optimizing the cardio respiratory fitness of an individual living organism wherein the optimal exercise intensity is calculated, and wherein said system comprises (a) means or sensors to measure the exercise intensity in real-time; (b) means or sensors to measure the biological response, preferably defined by heart rate parameters, to exercise intensity in real-time; (c) a processing unit that quantifies and models said biological response, preferably heart rate, mathematically in real-time, that predicts the future biological response, preferably heart rate, to exercise intensity and/or that calculates the desired individual exercise intensity; (d) an output device that reports the calculated exercise intensity to the individual.

Preferably, said system monitors the transition from the aerobic to anaerobic energy delivery phase by calculating by the processing unit in real-time the dynamic changes of the biological response to exercise intensity with mathematical models, particularly a dynamic databased model.

Preferably, the transition from the aerobic to anaerobic energy delivery system is assessed and/or predicted by monitoring the prediction error of a time invariant model of the biological response to exercise intensity.

Thus, a first aspect of the present invention relates to a method for evaluating and controlling the cardio respiratory fitness of an individual living organism in connection with an activity or exercise comprising (i) measuring one or more heart rate parameters and the intensity of the activity or exercise of said individual in real time; (ii) determining or predicting the lactate threshold of said individual by using a data base modelling technique to model the dynamic, individual and time variant response of heart rate to activity or exercise intensity in real time.

In one embodiment, said method comprises monitoring the changes in the system dynamics, model parameters or model prediction error when doing activities or exercising below or above the lactate threshold to determine the lactate threshold.

In another embodiment, the cardio respiratory fitness of said individual is determined or predicted during warm-up or during daily activities. Preferably, said method further comprises the determination of the time constant of the heart rate response to exercise intensity (wherein the time constant (TC) of a response is the time needed to achieve 63% of the steady state after onset of exercise).

In another embodiment, said method further comprises recalculation of the training protocol and/or exercise intensity.

Thus, a second aspect of the present invention relates to a system for evaluating and controlling the cardio respiratory fitness of an individual living organims comprising (i) means for measuring one or more biological and physiological variables of said individual, preferably the heart rate; (ii) means for measuring the activity or exercise intensity; (iii) a processing unit that, using a data based modelling technique relates and models the biological and physiological response of said individual to activity or exercise intensity and subsequently estimates or predicts the lactate threshold.

In one embodiment, said system of the present invention optionally further comprises (iv) an input unit to enter one or more physiological parameters which refer to the person's age, weight, height, gender or other physiological property.

Preferably, said means for measuring the biological and physiological variables of said individual is a hear rate monitor.

DESCRIPTION

DETAILED DESCRIPTION

Figure 1:
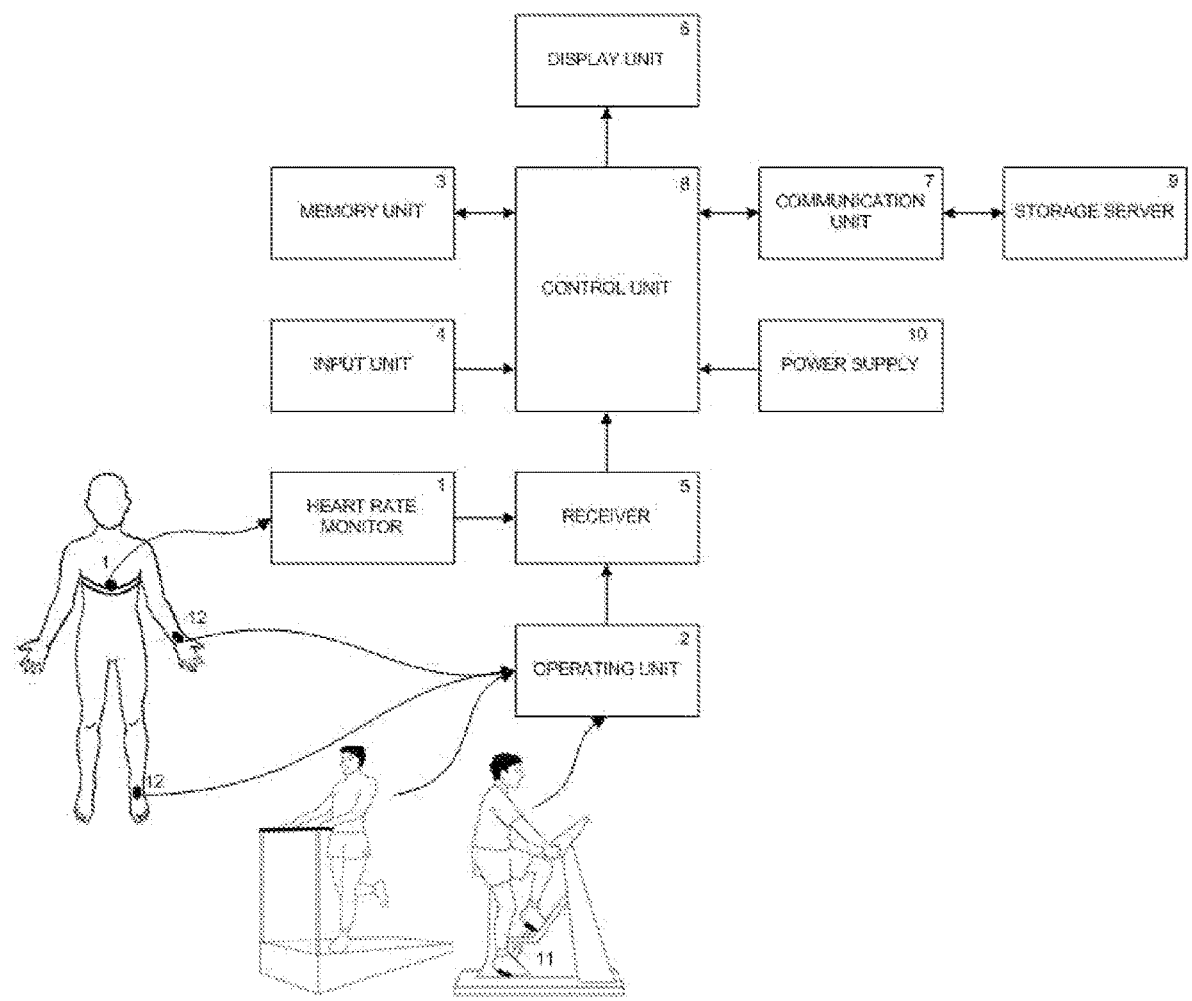
FIG. 1 is a diagram of an exercise system in accordance with the present invention.

The inventors developed a method, using a data based modelling technique, to determine in real time important biological and physiological variables related to cardio respiratory fitness and exercise intensity of an individual animal or human, particularly by measuring and continuously calculating the individual and time variant animal or human response to exercise intensity. The inventors developed a method to monitor and predict the transition between the aerobic and anaerobic training zones and, hence, the LT in real-time by detecting the dynamic change of the heart rate response to exercise intensity that occurs when an individual user exceeds his personal LT. The inventors also determined the cardio respiratory fitness based on a sub maximal step test, which can be performed before the normal (active phase of an) exercise as a warming up. The invention uses the individual cardio respiratory fitness to predict how the heart rate will respond to a certain exercise. Thus, individual models for every user (animal or human) are developed relating how the individual's heart rate responds to exercise intensity. This way it is possible to quantify the necessary exercise intensity to achieve an effective workout.

In this context, knowing the relationship between heart rate and exercise intensity according to the real time individual model indeed allows steering the exercise intensity and, hence, the heart rate to a desired level (or trajectory). This desired target HR level/trajectory is something a trainer/expert could define.

In the context of the present invention, an "exercise" relates to all activities or physical performance where cardio vascular condition plays a role. "Exercise" as used herein is synonymous to the term "activity". Thus, exercise as used herein, refers to daily activities, like walking stairs, running, carrying loads etc, as well as to a sporting performance, i.e. a physical performance, part of which may be carried out at a workload level exceeding the anaerobic level, whereby lactate is accumulated in the muscles of the person's body. The application of the invention is not only restricted to the moment of the active phase of the exercise. It can be assumed that the exercise divides into the following phases: warm-up, active phase, recovery phase when the exercise is preceded and followed by a rest. Different phases can be defined and distinguished, for instance, on the basis of heart rate levels and/or workload levels, as known by a person skilled in the art. Particularly, the present invention is applicable during warm-up.

The term "status" of an individual human or animal is an indication of how an individual living organism acts, behaves, and/or feels at a given moment and is particularly used herein to refer to the cardio respiratory fitness of individual human beings or individual animals (e.g. horses).

The present invention comprise the use of data based modelling technique to monitor, predict and/or control the individual and time variant response of said living organism, preferably an individual human, to exercise intensity. In this technique a biological system is described using (abstract) mathematical models for which the model characteristics and parameters are biologically and physiologically interpreted. In the context of the present invention, in order to determine or predict the transition between the aerobic and anaerobic training zone and to model the cardio respiratory fitness, it is necessary to determine the biological variables that are involved in the cardio respiratory system and the biological variables that are affected by the cardio respiratory system. By building a model based on the dominant biological or physiological variables (i.e. the variables that have the greatest impact on the system), the transition between the aerobic and anaerobic training zone and the cardio respiratory fitness can be effectively monitored, assessed and/or predicted.

In addition, the use of a data based on-line modelling technique, based on real-time information, measured dynamically on inputs and outputs of the biological system (i.e. the exercising body) offers the advantage that such models can have a simple structure with a low number of parameters that can be updated in real time, yet surprisingly enable accurate prediction of the dynamic and time variant behaviour of an individual, complex living system. Thanks to their simple structure and low number of parameters, said models can be readily implemented in (real-time) process control means, at commercially acceptable costs.

In the context of the present invention the data based modelling technique can be applied to develop any model structure that allows monitoring, estimating and displaying in real-time the time variant behaviour of said biological or physiological parameter of an individual living organism (preferably human) during exercise, in particular one or more heart rate parameters, more specifically the heart rate response to exercise intensity. In particular, the time varying behaviour of the heart rate is due to the fact that the heart rate will not always respond in the same way on a certain exercise level. A specific exercise in the early morning may have a different impact on the body than that same specific exercise late in the afternoon. The changing individual cardio respiratory fitness is one of the factors that form the basis of the time varying behaviour of the heart rate response to exercise intensity. Advantageously, the present invention provides a simple way to monitor the cardio respiratory fitness during an exercise by monitoring the transition between the aerobic and anaerobic training zone and/or by predicting this transition based on a simple warm-up protocol. Furthermore, the methods and systems of the present invention take cardiac drift into account, because the model can re-estimate this transition in real-time.

In a preferred embodiment of the present invention a mathematical model is developed that describes how one or more heart rate parameters, most preferably the heart rate, respond to a change in exercise intensity. The present mathematical model only describes the physical part of the heart rate response. This means that the mental part, which also influences the heart rate during training, is removed from the heart rate response (for the mental part see e.g. WO2008003148).

Preferably, the parameters of the model include one or more heart rate parameters representing the heart rate of said individual living organism, such as the heart rate calculated from heart beat frequency, standard deviation of the heart rate, change rate of the heart rate or a similar parameter that can be calculated from the heart rate. Preferably, the model's input parameters comprise one or more parameters related to the exercise intensity, such as the runner's speed, resistance of an exercise bike or activity measured with an acceleration transducer or the like. Other optional input parameters may include one or more physiological parameters which refer to the living organism's age, weight, height, gender or desired exercise intensity (or training goal).

Thus, a first aspect of the present invention provides methods for evaluating and controlling the cardio respiratory fitness of an individual living organism, such as an individual human or animal, in connection with an exercise comprising the use of a data based modelling technique to determine, estimate or predict fitness related biological and physiological variables, preferably the lactate threshold, of the exercising individual. Preferably, said method of the present invention further comprises measuring and modelling the individual and time variant response of said living organism to exercise intensity. More preferably, said individual and time variant response of said living organims is one or more heart rate parameters, particularly the heart rate, of the exercising individual.

Thus, in a preferred embodiment, the present invention provides a method for evaluating and controlling the cardio respiratory fitness of an individual living organism comprising (i) measuring and modelling in real time the response of one or more heart rate parameters of the exercising individual, particularly the heart rate, to the exercise intensity using a data based modelling technique and (ii) determining the changing system dynamics of the dynamic heart rate response to exercise intensity. The changing system dynamics upon transition between the aerobic and the anaerobic training or exercise zone can be reflected by changes of the model characteristics, such as the model order, the model parameters, the model prediction error . . . .

In this context, the monitoring and prediction of the transition between the aerobic and the anaerobic training zone, or stated differently the lactate threshold, comprise the use of a data based model in which the changing dynamics of the heart rate response to training intensity is continuously calculated. These changing dynamics are indicators for the switch between the aerobic and the anaerobic training zone, which occurs at the MLSS. The present invention thus allows an accurate and easy estimation of the MLSS. This knowledge is essential for an excersing living organism, such as an athlete, because exercise just below the MLSS helps to increase the aerobic capacity.

This invention monitors the changing dynamics of the heart rate response to exercise, which occurs at the MLSS. This can be explained by the fact that the energy delivering mechanism is different before the MLSS than after the MLSS.

Yet another preferred embodiment of the present invention relates to the assessment of the cardio respiratory fitness of an individual living organism, such as an animal or human, based on a sub maximal step test. The dynamic heart rate response to exercise contains all the information about the cardio respiratory fitness and data based models are used to calculate it out of the real-time collected data. This sub maximal test can be performed before the normal exercise as a warming up. It is understood that in this sub maximal test the exercising living organism (preferably human) does not reach the lactate threshold and hence, remains in the aerobic phase. The invention uses the individual cardio respiratory fitness to predict how the heart rate will respond to a certain exercise.

Thus, the present invention also provides a method for evaluating and controlling the cardio respiratory fitness of an individual comprising (i) measuring and modelling in real time the response of one or more heart rate parameters of the exercising living organism, particularly the heart rate, to the exercise intensity using a data based modelling technique and (ii) representing the changing system dynamics of the dynamic heart rate response to exercise intensity, e.g. by the Time Constant of the heart rate response (i.e. the time needed to achieve 63% of the steady state after onset of exercise) as a parameter relating to the fitness level of the individual.

Based on the knowledge of the individual cardio respiratory fitness and the individual modelled relation between heart rate and exercise intensity, it is possible to predict how the heart rate will respond to a certain exercise. This allows preparing optimal exercise schedules in order to achieve an effective workout or training The method of the present invention can be integrated in devices with a suitable processor for performing the calculations such as heart rate monitors, mobile phones, personal computers, portable GPS, PDA devices and fitness equipment. The device is able to send the data to a remote server to store all the data and to calculate the progress with specific software. Preferably, this device is also able to provide feedback to the exercising individual to optimise his exercise protocol.

Thus, another object of the present invention provides a system for evaluating and controlling the cardio respiratory fitness of an individual comprising (i) means for measuring the biological and physiological variables, preferably a heart rate monitor (1); (ii) means for measuring the exercise intensity (2), such as based on power cranks (11), accelerometers (12) or sensors to assess speed; and (iii) a processing unit that, using a data based modelling technique, relates the heart rate response to training intensity of the individual exercising person, and based on that individual, real-time model estimates and predicts fitness related biological and physiological parameters, in particular the lactate threshold, and subsequently is able to calculate the needed exercise intensity.

A heart rate monitor is a device employed in sports and medicine, which measures (human) heart rate information either from an electrical impulse transmitted by the heart or from the pressure produced by the heart beat on an artery. Generally, the heart rate monitors have a structure comprising an electrode belt to be fitted around the user's chest measuring the heart rate by means of two or more electrodes. The electrode belt transmits the measured heart rate information inductively as one or more magnetic pulses per heart beat, for instance, to a wrist-worn receiver unit. On the basis of the received magnetic pulses, the receiver unit calculates the heart rate and, when needed, other heart rate variables, such as moving standard deviation of the heart rate. Often, the receiver unit, i.e. the wrist monitor, also comprises a display for displaying the heart rate information to the exercise performer and a user interface for the use of other facilities of the heart rate monitor.

The system of the present invention may optionally further comprise (iv) an input unit (4), to enter one or more physiological parameters which refer to the living organism's (person's) age, weight, height, gender or other physiological property.

In addition, the system of the present invention may further comprise a memory unit (3), receiver (5), display unit (6), communication unit (7), storage server (9) and power supply (10).

Referring now specifically to the drawings, an exercise system according to the present invention is illustrated in FIG. 1 and comprises a heart rate monitor (1), operating unit (2), memory unit (3), input unit (4), receiver (5), display unit (6), communication unit (7), control unit (8), storage server (9) and power supply (10).

The operating unit (2) is an operation device that receives the exercise intensity exerted by the user. These can be power cranks (11) if the device is used for cycling and it can be accelerometers (12) or sensors to assess speed if the device is used for runners.

The memory unit (3) stores all the data that is measured during the exercise. This data is also shown during exercise on the display unit (6).

The input unit (4) is a unit were the user can load his personal anthropometric data, his cardio respiratory fitness parameters and the wanted exercise goal. It may include parameters as height, age, weight, gender, predefined cardio respiratory fitness.

The receiver unit (5) receives all necessary data that is needed for optimal exercise. This comprises biological measurements as heart rate measured by a heart rate monitor (1) and data collected by the operating unit (2) and/or the input unit (4).

The communication unit (7) is a device that sends the data to a storage server (9). This can be done wireless or with cable.

Figure 2:
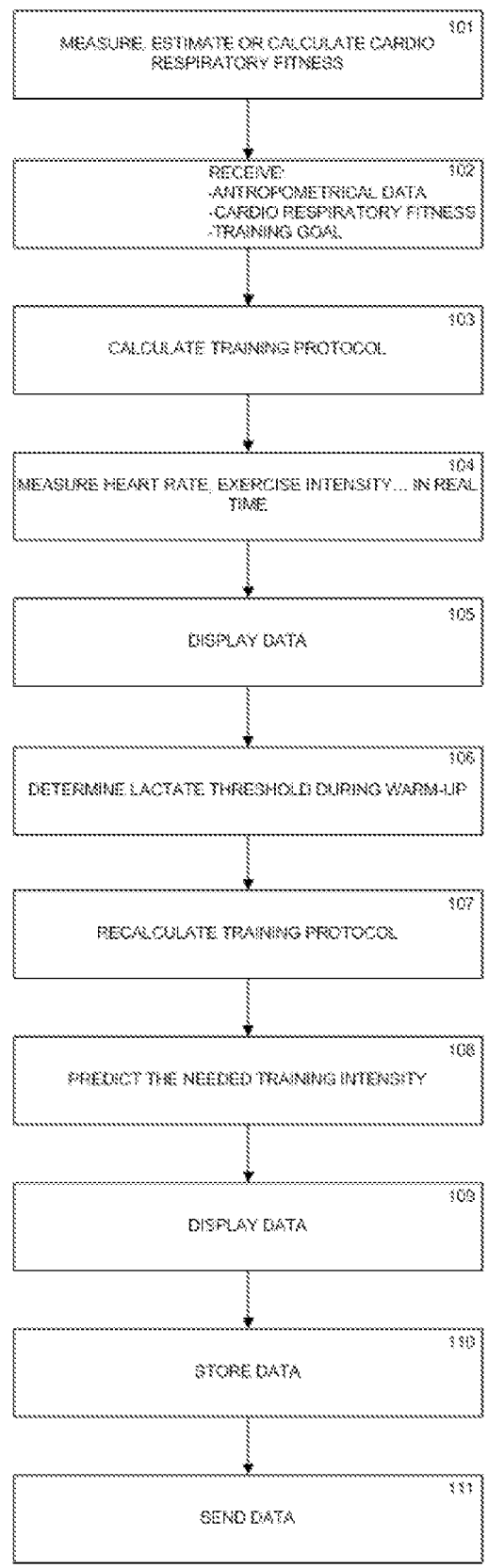
FIG. 2 is a flowchart of the control method of the exercise system in accordance with the present invention.

The control unit or processing unit (8) connects all the previous units and it calculates the needed exercise intensity. With reference to FIG. 2, the control unit (8) performs one or more of the following steps to calculate the needed exercise intensity: receive anthropometrical data, cardio respiratory fitness parameters and exercise goal (102), measure heart rate and exercise intensity in real-time during exercise (104), display heart rate and exercise intensity in real-time during exercise (105), determine cardio respiratory fitness during exercise (106), recalculate exercise protocol based on cardio respiratory fitness (and based on the generated model relating heart rate response to exercise intensity) (107), predict the needed exercise intensity (108), display the needed exercise intensity to fulfil the exercise protocol (109), store all the data (110) and send the data to a storage server (111). Thus, particularly in step (106), the processing unit develops an individual model linking the dynamic heart rate response of the training individual to exercise intensity in real-time with data-based modelling techniques. This individual model also allows recalculating the exercise protocol & the needed exercise intensity to reach a certain training goal and/or to achieve an effective workout or training In the context of the present invention, a "processing unit" includes a device using one or more processors, microcontrollers and/or digital signal processors having the capability of running a "program" which is a set of executable machine code. Processing systems include computers, or "computing devices" of all forms (desktops, laptops, PDAs, servers, workstations, etc.), as well as other processor-based communication and electronic devices such as cell phones, tablets, personal data assistants, etc. Such processing systems may be discrete units, or may be formed of multiple components, which may be networked or otherwise capable of being placed in operative communication with one another, at least at needed intervals. A "program" as used herein, includes user-level applications as well as system-directed applications or daemons.

In the step of receiving the cardio respiratory fitness parameters (102), the user can type in a predefined cardio respiratory fitness parameter and an exercise goal (101) in the input unit (4). These parameters are used to calculate a basis exercise intensity to obtain the wanted exercise goal (103) as done by other systems. This cardio respiratory fitness parameter will later be optimized during the exercise (106). The cardio respiratory fitness parameter can be measured by other methods as seen in the state-of-art, but it can be measured by our invention as referenced in FIG. 3.

Figure 4:
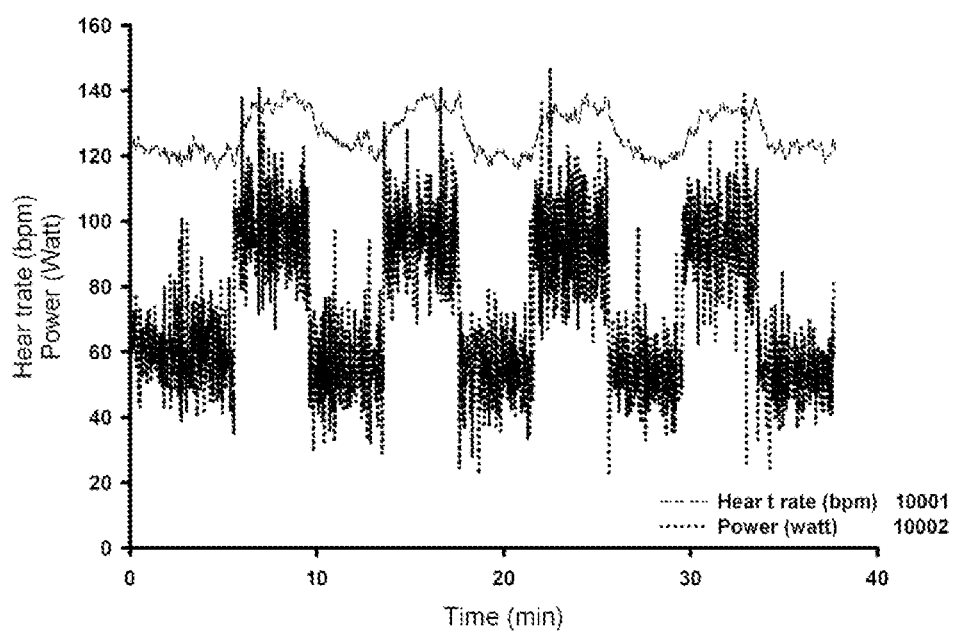
FIG. 4 is a schematic overview of the exercise protocol that is used to predict the lactate threshold.

When the exercise starts, the heart rate monitor (1) measures the heart rate during exercise (104) and the operation units (2) measure the exercise intensity during exercise (104). All these data can be shown on the display (105). During the warm-up, a special test protocol, as referenced in FIG. 4, is used by the methods and system of the present invention to estimate the real individual cardio respiratory fitness (106) as referenced in FIG. 5. This real cardio respiratory fitness is used to recalculate the exercise protocol (107). Therefore, the needed exercise intensity is predicted (108) to obtain the wanted exercise goal, based on the individual estimated cardio respiratory fitness and with the knowledge of how the heart rate individually responds to exercise intensity (according to the modelled dynamic heart response to training intensity of that individual). The required exercise intensity to fulfil the exercise is then displayed (109). All the measured data, calculated cardio respiratory fitness parameters and exercise protocols are then stored (110) in the memory unit (3) and send (111) to the storage server (9) by the communication interface (7).

Figure 3:
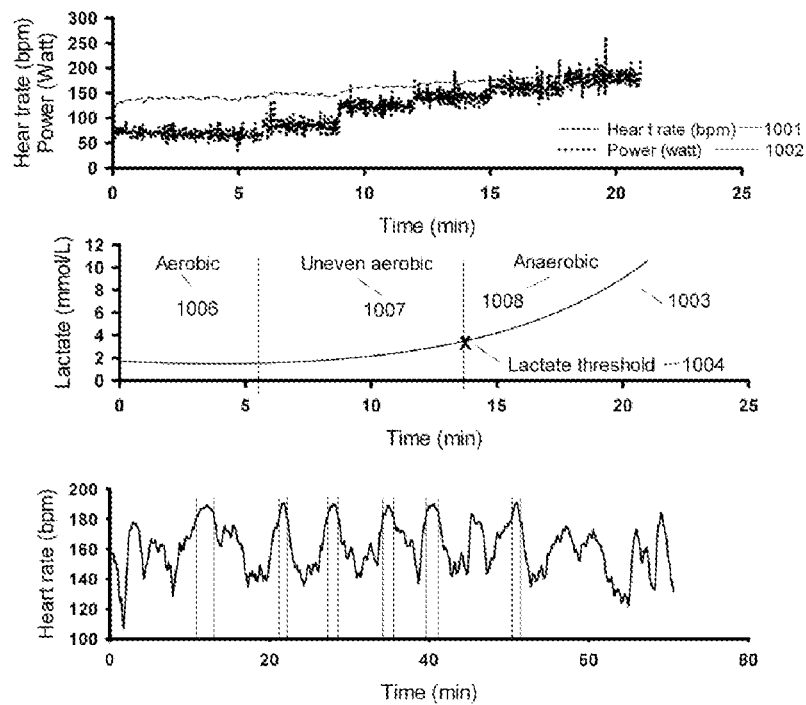
FIG. 3 is a schematic representation of a step test until exhaustion with the corresponding lactate measurements and energy zones together with the changing dynamic parameters and the prediction error that are used to estimate the lactate threshold.
Figure 3:
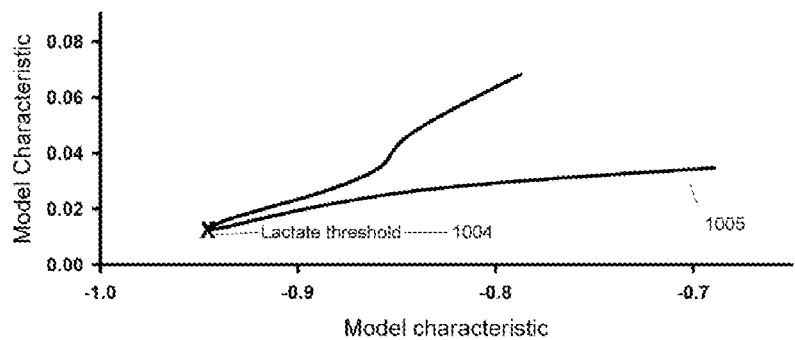
Figure 3:
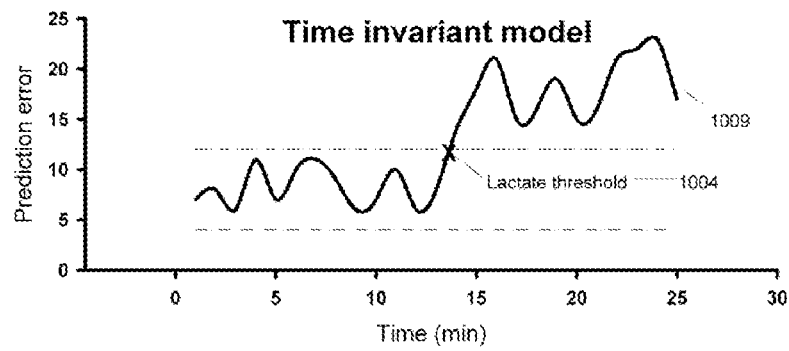

With reference to FIG. 3, let us consider the heart rate curve (1001), the exercise intensity curve (1002), the lactate curve (1003) and the system dynamics curve (1005) illustrating how the data can be used to obtain the lactate threshold (LT) (1004), which is an indicator for the cardio respiratory fitness. In prior state-of-art, the LT (1004) is measured by utilising a step test until exhaustion (1001 and 1002) with accompaniment lactate measurements (1003).

Lactate is one of the end products that are formed to create energy during exercise. The energy is supplied in the form of adenosine triphosphate (ATP). When ATP is converted into adenosine driphosphate (ADP), energy is released that the muscles can use. ATP is formed in the glycolysis by conversing glucose into pyruvate.

Glucose+2Pi+2ADP+2NAD$^+$→2pyruvate+2ATP+ 2NADH+2H$^+$+H2O

Next, the formed pyruvate can be converted into acetyl coenzyme A (CoA).

Pyruvate+NAD$^-$+CoA →acetyl CoA+CO2 +NADH

Acetyl CoA is converted into 2 CO2, 1 GTP en 8 e- in the citric acid cycle. This cycle takes place in the mitochondria of the muscles. The 8 e- are converted into energy by means of oxidative phosphorylation (9 ATP units).

When there is not enough oxygen present in the muscles for the oxidative phosphorylation, the energy is produced in a different way. The pyruvate is then converted into lactate through the lactic acid fermentation process.

Pyruvate+NADH+H$^+$→NAD$^+$+lactate

In this process NADH is converted back into the energy rich form NAD+. This NAD+ can be utilised again in the glycolysis to free up new energy. Lactate is the end product of this metabolic reaction and it cannot be removed from the body, but is broken down broken down in the brains, heart, kidney and skeletal muscle by oxidize lactate into CO2 and H20.

The glucose in muscle tissue is consumed much slower during aerobic conditions than during anaerobic conditions. Therefore, aerobic efforts can be sustained much longer.

The aerobic and the anaerobic system do not work separately in the human body, so different phases can be observed during exercise. For small efforts, the lactate concentration stays more or less the same as the concentration at rest, because enough oxygen can be transported to the active muscles. This phase is called "aerobic phase" (1006). When exercise intensity continues to rise, the lactate concentration starts to increase and will stabilize around a steady state if the exercise intensity stops increasing. In this case, the lactate removal, by oxidation into CO2 and H2O, is in equilibrium with the lactate production. This phase is called "uneven aerobic phase" (1007). At a specific effort, the lactate production will become larger than the lactate removal. The lactate concentration will keep rising even if this effort is maintained. That phase is called the "anaerobic phase" (1008).

The transition point between the "uneven aerobic phase" (1007) and anaerobic phase (1008) is called the LT (1004). This is actually the biggest effort that can be maintained with the lactate production in equilibrium with the lactate removal. So, the LT is defined as the highest exercise intensity that can be maintained for at least twenty minutes without a significant rise of the lactate concentration [Hoogeveen et al., International Journal of Sports Medicine, 1999, 20 (2) 114-117].

The heart rate response to exercise will be different when the exercise intensity exceeds the LT and this will be reflected in different system dynamics. This change can be picked up by the system and method of the present invention, because the model characteristics will change to adapt to the changing system dynamics. This technique can be used during normal training to differentiate between aerobic and anaerobic training zones (FIG. 3).

The present invention monitors the changing dynamics (1005) of the heart rate response to exercise, which occurs at the LT. This can be explained by the fact that the energy delivering mechanism is different before the LT than after the LT. In the developed method, the dynamic heart rate response to power output is modelled in real-time with data-based models. Possible model structures that can be used include for example the ARX model structure and the OE model structure, but other model structures are also applicable. ARX is an "auto-regressive model with exogeneous input". The autoregressive part corresponds with $y_k$ $A(z^{-1})$ and the additional inputs $u_k$ $B(z^{-1})$ are the exogenous variables. The model is an equation of the following form:

$$y_k+a_1y_{k-1}+\ldots+a_{na}y_{k-na}=b_0u_{k-nk}+b_1u_{k-nk-1}+\ldots+b_{nb}u_{k-nk-nb-1}+e_k \quad (1)$$

Equation 1 determines the output y at time k based on a number of previous inputs $u_{k-i}$ and outputs $y_{k-i}$. The structure is completely determined by the three integers $n_a$, $n_b$ and $n_k$. $n_a$ represents the number of poles of the system and $n_b$ corresponds to the number of zeros of the system. $n_k$ is the time delay (or dead time) of the system.

Equation 1 is often written under the ARX transfer function form:

$$y_k = \frac{B(z^{-1})}{A(z^{-1})}u_{k-s} + \frac{1}{A(z^{-1})}e_k \quad (2)$$

with,

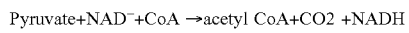

$$A(z^{-1})=1+a_1z^{-1}+\ldots+a_{na}z^{-n} \quad (3)$$

$$B(z^{-1})=b_0+b_1z^{-1}+\ldots+b_{nb}z^{-m} \quad (4)$$

The OE or "output-error model structure is of the following form:

$$y_k = \frac{B(z^{-1})}{F(z^{-1})}u_{k-s} + e_k \quad (5)$$

With,

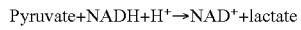

$$F(z^{-1})=1+f_1z^{-1}+\ldots+f_nz^{-n} \quad (6)$$

$$B(z^{-1})=b_0+b_1z^{-1}+\ldots+b_{nb}z^{-m} \quad (7)$$

The changing system dynamics can be reflected by changes of the model characteristics, such as the model order (or number of model parameters), the model parameters . . . . This is shown by curve 1005. In all the analysis, a clear difference between the two phases was found (1005) if two specific model characteristics were plotted in function of each other. Another method is to calculate a time invariant model at the beginning of the aerobic phase and to simulate or predict the heart rate for the remainder of the data. This model will introduce a prediction error (i.e. the difference between the predicted heart rate based on the model and measured heart rate) (1009) during the anaerobic phase, because of the different dynamics.

With reference to FIG. 4, let us consider the heart rate curve (10001), the exercise intensity curve (10002), illustrating the dataset that is needed during the warming up to predict the lactate threshold (LT), which is an indicator for the cardio respiratory fitness. The average time constant of the heart rate response over a total cycling session, could be linked to the fitness level of the participants. The time constant (TC) of a response is the time needed to achieve 63% of the steady state after onset of exercise. The time constant gives an idea of how fast the body reacts to the external load. A certain exercise intensity will impose less physical stress on the body of a fit person and thus the steady state heart rate for a step response will be reached faster.

Figure 5:
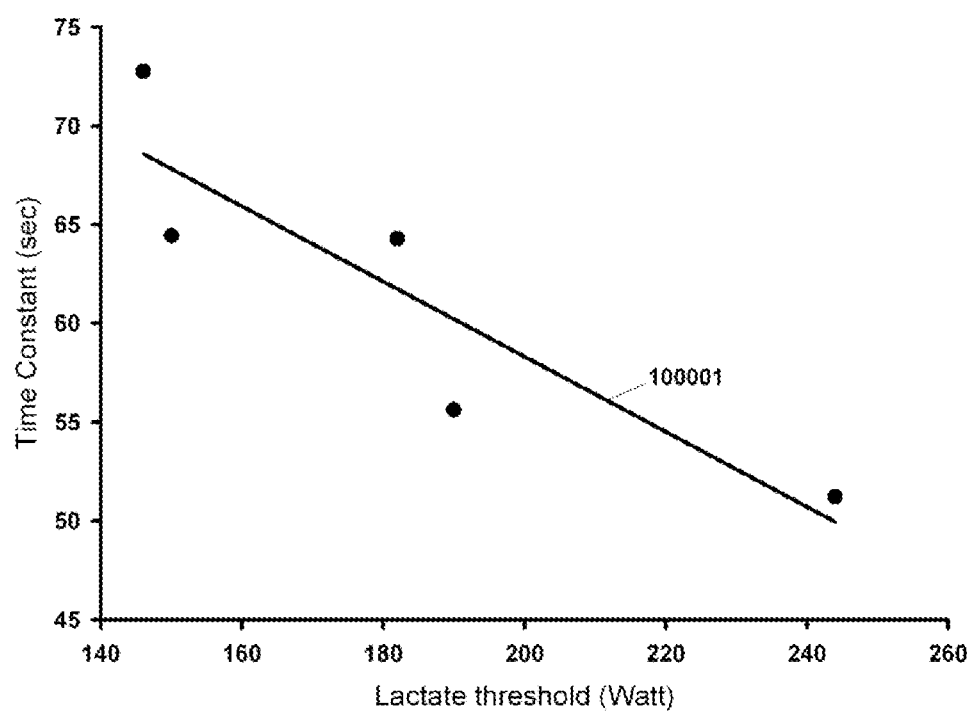
FIG. 5 shows the lactate threshold as function of the time constant that is calculated in one embodiment if the invention.

This was proven on fifty-four datasets taken from the daily exercise of professional athletes, junior athletes, a female athlete and one amateur cyclist. The time constants of the four subgroups differed significantly and were ordered in a manner that indicates an increasing fitness level: the amateur cyclist (120.4 sec), the female athlete (52.1 sec), the junior athletes (38.5±0.73 sec) and the professional athletes (30.6±4.5 sec). These findings were translated into a testing protocol for predicting the LT without the need of the step test until exhaustion. The step test until exhaustion was only utilized to obtain proof of concept. Next, four small sub maximal steps of the exercise intensity (10002) were applied. During these test, the heart rate (10001) and exercise intensity (10002) are monitored. In the developed method, the dynamic heart rate response to exercise intensity is modelled in real-time with data-based models as described above. The TC is calculated for the four steps and averaged over the whole dataset. This TC is then plotted, as shown in FIG. 5, against the measured LT of the corresponding test subjects. This yielded a curve (100001) which indicates a possible relationship between the TC and the LT. If these small sub maximal steps are incorporated in the warming up, this relationship (100001) can be used to estimate the LT of the users by calculating the TC during the warming up.

Other embodiments of the invention will be apparent to those skilled in the art from consideration of the specification and practice of the invention disclosed herein.

It is intended that the specification and examples be considered as exemplary only.

The invention claimed is:

1. A method for evaluating and controlling the cardio respiratory fitness of an individual living organism in connection with an activity or exercise comprising:
   (i) measuring in real time one or more heart rate parameters of the individual using a first sensor and an intensity of the activity or exercise of said individual using a second sensor;
   (ii) communicating said one or more heart rate parameters and the intensity of the activity or exercise from the first sensor and the second sensor to a processing unit;
   (iii) determining or predicting a lactate threshold of said individual in the processing unit by using a mathematical model to model an individual response of heart rate to activity or exercise intensity;
   (iv) outputting said determination or prediction of the lactate threshold from the processing unit to a display unit and to a storage server;
   wherein step (iii) comprises dynamically updating the mathematical model by using a dynamic data base modelling technique to model in real time a dynamic, individual and time variant response of the heart rate to activity or exercise intensity;
   wherein the dynamically updating the mathematical model comprises changing characteristics of the mathematical model; and
   wherein the mathematical model comprises an autoregressive model and/or an output-error model.

2. The method according to claim 1, further comprising a step of monitoring changes in system dynamics, model parameters or model prediction error when doing activities or exercising below or above the lactate threshold to determine the lactate threshold.

3. The method according to claim 1, wherein the cardio respiratory fitness of said individual is determined or predicted during warm-up.

4. The method according to claim 3, further comprising determining a time constant of the heart rate response to exercise intensity.

5. The method according to claim 3, further comprising recalculating a training protocol and/or exercise intensity.

6. A system for evaluating and controlling the cardio respiratory fitness of an individual living organism comprising:
   (i) means for measuring one or more biological and physiological variables of said individual living organism in real time, said one or more biological and physiological variables comprising a heart rate;
   (ii) means for measuring an activity or exercise intensity in real time;
   (iii) a processing unit that relates and models a biological and physiological response of said individual living organism to activity or exercise intensity in real time using a mathematical model and subsequently estimates a lactate threshold;
   (iv) a display unit that displays in real time one or more of said one or more biological and physiological variables, said activity or exercise intensity, and said lactate threshold;
   wherein the processing unit dynamically updates the mathematical model by using a data based modelling technique that relates and models in real time the dynamic, individual and time variant biological and physiological response of said individual to activity or exercise intensity and subsequently estimates or predicts the lactate threshold;
   wherein the dynamically updating the mathematical model comprises changing characteristics of the mathematical model; and
   wherein the mathematical model comprises an autoregressive model and/or an output-error model.

7. The system according to claim 6, further comprising (iv) an input unit to enter one or more physiological parameters which refer to the individual living organism's age, weight, height, gender or other physiological property.

8. The system according to claim 6, wherein said means for measuring the biological and physiological variables of said individual is a heart rate monitor.

* * * * *